United States Patent [19]

Sih

[11] Patent Number: 4,584,270

[45] Date of Patent: Apr. 22, 1986

[54] PROCESS FOR PREPARING OPTICALLY-ACTIVE 4-AMINO-3-HYDROXYBUTYRIC ACID

[75] Inventor: Charles J. Sih, Madison, Wis.

[73] Assignee: Wisconsin Alumni Research Foundation, Madison, Wis.

[21] Appl. No.: 573,247

[22] Filed: Jan. 23, 1984

[51] Int. Cl.⁴ .................. C12P 13/00; C12R 1/01; C07C 101/30; C07C 119/042
[52] U.S. Cl. .................... 435/128; 435/146; 435/280; 435/822; 435/830; 435/843; 435/863; 562/567; 558/410
[58] Field of Search ............... 435/146, 280, 128, 822, 435/830, 843, 863; 562/567; 260/453 AL

[56] References Cited

U.S. PATENT DOCUMENTS 3,823,069  7/1974  Miyaki .................. 435/280
4,371,618  2/1983  Cavazza ................ 435/128

FOREIGN PATENT DOCUMENTS 80827  6/1983  European Pat. Off. ........ 435/128
57-94295  6/1982  Japan .................. 435/280

*Primary Examiner*—Esther M. Kepplinger
*Assistant Examiner*—Shawn P. Foley
*Attorney, Agent, or Firm*—Howard W. Bremer

[57] ABSTRACT

The present invention relates to processes for preparing optically-active 4-amino-3-hydroxybutyric acid by asymmetrically cleaving one of the enantiotopic ester groupings of 3-hydroxyglutaric diester by the action of microbial enzymes to obtain a chiral monoacid which is readily converted into optically-active 4-amino-3-hydroxybutyric acid by chemical means.

9 Claims, No Drawings

PROCESS FOR PREPARING OPTICALLY-ACTIVE 4-AMINO-3-HYDROXYBUTYRIC ACID

DESCRIPTION

1. Field of the Invention

The present invention relates to processes for preparing a compound which can function as a key intermediate in the preparation of L-carnitine and related compounds.

More specifically, this invention relates to processes for preparing optically active 4-amino-3-hydroxybutyric acid.

2. Background Art

4-Amino-3-hydroxybutyric acid, characterized by the structural formula

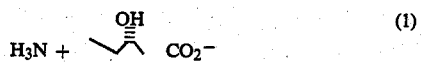

was first synthesized by M. Tomita.

[Z. Physiol. Chem., 124, 253 (1923)] in 1923 and was detected in rat brain by T. Hayaishi [J. Physiol., 145, 570 (1959)] in 1959. The remarkable importance of this compound stems from its biological function as a neuromodulator in the mammalian central nervous system [M. Otsuka et al., J. Neurochem., 18, 287 (1971)]. Moreover, the metabolic correlation of 1 with 4-aminobutyric acid and thus with glutamic acid and glutamine justifies interest concerning its use in the treatment of epilepsy [unlisted drugs, 16, 6K (1964) and 25, 1411 (1973)]. Furthermore, it is well documented that (R)-4-amino-3-hydroxybutyric acid is a valuable precursor to the important compound, L-carnitine.

Four methods have been reported for the synthesis of compound (1) above.

The first of these methods uses a two carbon atom-containing material (e.g. glycine) as the starting material but suffers from the difficulty of preparing the key intermediate in the process, 4-phthalimidocrotonic acid [J. Org. Chem., 19, 1589 (1954)].

The second method [Z. Physiol. Chem., 124, 253 (1923)] consists of reacting phthalimide with epichlorohydrin to form 1-chloro-2-hydroxy-3-phthalimidopropane, followed by exchange with cyanide, and final hydrolysis to compound 1. In spite of its industrial application [M. Hayaishi et al., Japanese Pat. 772 (1958); Chem. Abstr., 53, P1172d (1959); A. Gallardo, Spanish Pat. No. 278,780 (1963); T. Hayaishi, French Pat. No. 1,348,105 (1964)], this method suffers from serious ecological limitations due to the toxicity of epichlorohydrin and cyanides.

The third method entails a four-step reaction sequence, namely, bromination of the ethyl acetoacetate, reduction of the keto group, displacement of the halogen with ammonium hydroxide, the final hydrolysis of the ester [f. D'Alo and A. Masserini, Farmaco, Ed. Sci., 19, 30 (1964)]. However, the low reactivity of ethyl 4-bromo-3-hydroxybutyrate to nucleophilic displacement resulted in low overall yield.

To circumvent this problem, a fourth method was developed [M. Pinza and G. Pifferi, J. Pharm. Sci., 67, 120 (1978)] using 4-bromocrotonic acid since the allylic bromide in 4-bromocrotonic acid is more reactive towards nucleophilic displacement.

In all the above syntheses the resulting 4-amino-3-hydroxybutyric acid (1) is in its racemic form. This racemate was however separated by a tedious and expensive resolution procedure [M. Tomita and Y. Sendju, Z. Physiol. Chem., 169, 263 (1927)]. The (R) form of 1 is especially useful because it can be readily converted into the important compound L-carnitine by methylation [T. Keneko and R. Yoshida, Bull. Chem. Soc. Japan, 35I, 1153 (1962)].

DISCLOSURE OF INVENTION

The present invention relates to processes for producing optically-active 4-amino-3-hydroxybutyric acid which can serve as a key intermediate for the preparation of related compounds such as L-carnitine. Specifically, it relates to a process for asymmetrically cleaving one of the enantiotopic ester groupings of 3-hydroxyglutaric diester by the action of microbial enzymes. The resulting chiral monoacid can be readily converted into optically-active 4-amino-3-hydroxybutyric acid by chemical methods.

It is an object of this invention to produce optically-active 4-amino-3-hydroxybutyric acid in good yield through a combination of microbiological and chemical processes.

A further object of this invention is to provide an improved process for synthesizing (R)-4-amino-3-hydroxybutyric acid, a key intermediate for the preparation of L-carnitine, from readily available moderate cost raw materials.

Another object of this invention is to provide processes for preparing optically-active 4-amino-3-hydroxybutyric acid from optically-active 3-hydroxy-glutaric monoester via rearrangements to an electron-deficient nitrogen atom.

Still another object of the present invention is to provide a process for producing optically-active 3-hydroxy-glutaric monoester.

These and other objects of the present invention will become apparent from the following description.

BEST MODE FOR CARRYING OUT THE INVENTION

Although asymmetric hydrolysis of diethyl or dimethyl β-hydroxy glutarate by α-chymotrypsin was reported [S. G. Cohen and E. Khedouri, J. Am. Chem. Soc., 83, 4228 (1961)], the reaction rate of this hydrolysis is very slow. Consequently, virtually a stoichiometric amount of α-chymotrypsin is required to complete the reaction (substrate to enzyme ratio was 2:1), which makes it a very costly process. Also, while both (+) and (−)methyl hydroxy β-acetoxy glutarate had been prepared by chemical resolution methods [Arkiv fur Kemi, Bd 10, nr 4, 135 (1956)], these processes are tedious and the yield was relatively low. In contrast, by employing the hydrolytic action (esterases) of microbial enzymes in accordance with the process of the present invention, the asymmetric hydrolyses can be accomplished to yield either the (+) or (−) β-hydroxy glutaric monoester more economically.

Broadly this invention comprises the use of the microbial esteratic enzyme, carboxyesterase, to catalyze the asymmetric hydrolysis of β-hydroxy glutaric diester having the formula: $RO_2CCH_2-CHOHCH_2CO_2R$, where R is $CH_3$, $CH_2CH_3$.

It has been found that any microorganism which elaborates the desired carboxyesterase is capable of functioning to catalyze this asymmetric hydrolysis. Particularly suitable are those microorganisms to the genera Arthrobacter, Acinetobacter, Citrobacter, Corynebacterium, Mycobacterium, and Rhodococcus.

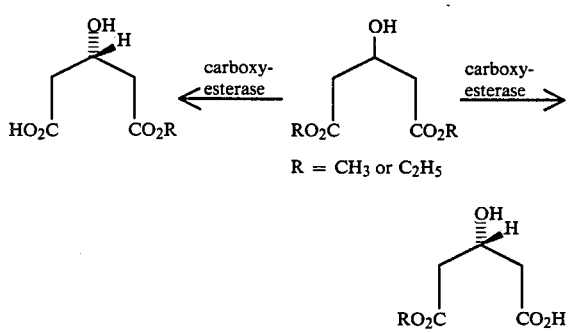

After protecting the hydroxyl function of the resulting optically-active β-hydroxy glutaric monoester, the β-acetoxy glutaric monoester may then be subjected to rearrangements via a nitrene (electron deficient) intermediate, which invites migration of the alkyl group with its pair of electrons from carbon to nitrogen yielding an isocyanate. The desired amine is obtained upon alkaline hydrolysis of the isocyanate.

The following is a representative schematic of the reaction steps of this process:

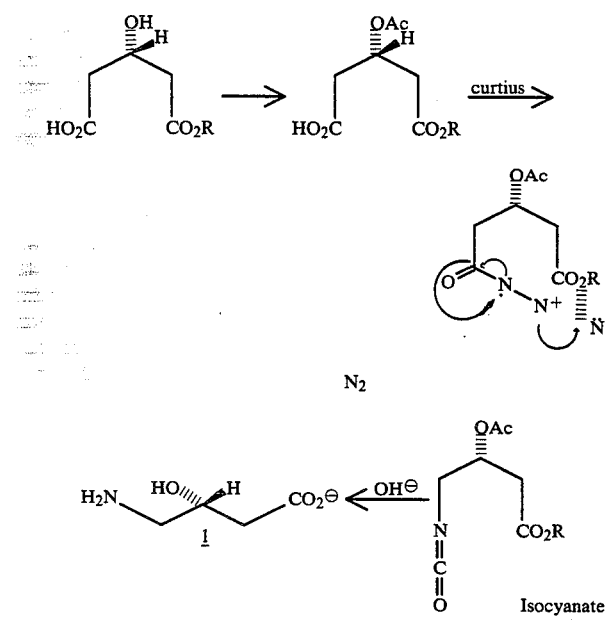

The foregoing process, as exemplified by the above scheme, is subject to numerous variations. It will be obvious to those skilled in the art that mechanistically similar rearrangements such as Hofmann, Schmidt and Curtius can all be used to effect this transformation. For the sake of convenience, we have selected the Curtius reaction to illustrate that such rearrangement may be achieved on a highly functionalized substrate in reasonable yields.

Microorganisms which have the desired carboxyesterase activity are well known in the microbiological art and any of such microorganisms can be employed in conducting the process of the present invention [see K. Kieslich, "Microbial Transformations of Non-Steroid Cyclic Compounds" (Georg Thieme Publishers, Stuttgart, 1976)] with any of the genera of microorganisms specifically described herein being particularly applicable.

The β-hydroxy glutaric diester can be incorporated in a nutrient medium of standard composition in which such organisms are cultivated and the usual conditions of fermentation can then be employed to effect the hydrolytic transformation. Alternatively, the active principle can be removed from the growing culture of the microorganism, for instance by lysis of the cells of release the enzymes, or by suspension of the resting cells in a fresh aqueous medium. Since this hydrolytic transformation requires no coenzymes, the cells and the enzyme are uniquely suited for immobilization to further reduce the cost of the process. In any of these techniques, an ester function will be asymmetrically cleaved, so long as the active enzyme elaborated by the microorganism is present. Of course, the temperature, time and pressure conditions under which the contact of the β-hydroxyglutaric diester with the hydrolytic enzyme is carried out are interdependent as will be apparant to those skilled in the art. For instance, with gentle heating and at atmospheric pressure, the time required will be less than if it progresses at room temperature under conditions otherwise the same. Of course, neither, temperature, nor pressure, nor time, should be so great that it results in the substrate being degraded. Where a growing culture of the organism is being used, the process conditions should also be sufficiently gentle so the organism is not killed before it elaborates sufficient proteolytic enzymes to permit destruction of the carboxyesterase enzyme. Generally, at atmospheric pressure, the temperature can range from about 10° C. to about 35° C., and the time from about 12 hours to about 10 days.

Each of the products produced in accordance with the following examples was identified as to chemical structure through the use of nuclear magnetic resonance (nmr), infrared spectra, and by thin layer chromatographic mobilities. The optical purity and the absolute configuration of the product were established by comparison of their optical rotation values with those reported in the literature and further confirmed by conversion into L-carnitine.

EXAMPLE 1

A. Fermentation. Surface growth from a one week old agar slant of Arthrobacter sp. (ATCC 19140) grown on an agar of the following composition:

|  | Gms |
|---|---|
| Agar | 20 |
| Bacto-beef extract | 3 |
| Bacto-peptone | 5 |
| (Sterilized 15 min at 20 p.s.i.) | | was suspended in 5 ml of an) 0.85% saline solution. One ml portions of this suspension were used to inoculate a 250 ml Erlenmeyer flask (F-1 stage) each containing 50 ml of the following medium (Difco nutrient broth):

|  | Gms |
|---|---|
| Bacto-beef extract | 3 |
| Bacto-peptone | 5 |
| Distilled water, q.s. | 1 liter |
| pH 6-8 (sterilized for 15 min at 30 p.s.i.) | |

The flasks were incubated at 25° C. on a rotary shaker (250 cycles/min—2" radius) for 24 hours, after which a 5% by volume transfer was made to a 2 liter Erlenmeyer flask containing 500 ml of Difco nutrient broth. Simultaneously, 2.2 g of diethyl-3-hydroxyglutarate (Aldrich) in 0.2 ml of 10% Tween 80 was added resulting in a final substrate concentration of 0.2%. The F-2 stage flasks were then incubated for an additional 48 hours under the conditions used in the incubation of the F-1 stage flasks.

B. Isolation. 48 hours after addition of the substrate, the F-2 stage was terminated by the addition of 6N HCl until pH of the medium is lowered to 2. The contents were filtered through a pad of celite and the filtrate was extracted with ethyl acetate (3×500 ml). The combined organic extracts were dried over sodium sulfate and concentrated in vacuo to give a residue (2.7 g). This residue was chromatographed over a silica gel (MN Kieselgel 60, Brinkmann) column (1.2×40 cm). The column was eluted with a solvent system comprised of hexane-ethyl acetate (1:1) to yield 1.44 g of ethyl hydrogen-3(S)-hydroxyglutarate, $[\alpha]_D^{25} + 1.5°$ (c, acetone).

C. The progress of the microbiological hydrolyses of diethyl-3-hydroxyglutarate may be followed by thin-layer chromatographic analyses using Brinkmann 20×20 cm (EM) plates (0.25 mm thickness) of silica gel containing PF254 indicator. The solvent system used was: hexane-ethyl acetate-acetic acid (10:10:1).

EXAMPLE 2

The procedure of Example 1 was repeated using dimethyl-3-hydroxyglutarate as the substrate and obtaining monomethyl-3(S)-hydroxyglutarate, $[\alpha]_D + 1.4°$ (c, 2.1, acetone) as a product.

EXAMPLE 3

The procedure of Example 1 was repeated using the microorganism *Corynebacterium equi* (IFO-3730) to obtain monoethyl-3(S)-hydroxyglutarate, $[\alpha]_D + 1.5°$ (acetone), in 85% yield.

EXAMPLE 4

The procedure of Example 1 was repeated using the microorganism Mycobacterium sp. (NRRL 15051) to obtain monoethyl-3(S)-hydroxyglutarate, $[\alpha]_D + 1.5°$ (acetone), in 50% yield.

EXAMPLE 5

The procedure of Example 1 was repeated using the microorganism *Rhodococcus equi* (ATCC 21690) to obtain monoethyl-3(S)-hydroxyglutarate, $[\alpha]_D + 1.4°$ (acetone), in 60% yield.

EXAMPLE 6

The procedure of Example 3 was repeated except dimethyl-3-hydroxyglutarate was used as the substrate and obtaining monomethyl-3(S)-hydroxyglutarate, $[\alpha]_D + 1.4°$ (acetone) as the product.

EXAMPLE 7

The procedure of Example 5 was repeated except dimethly-3-hydroxyglutarate was used as the substrate and obtaining monomethyl-3-(S)-hydroxyglutarate, $[\alpha]_D + 1.3°$ (acetone) as the product.

EXAMPLE 8

The procedure of Example 1 was repeated using the microorganism *Acinetobacter lowfii* (ATCC 29064) to obtain monoethyl-3(R)-hydroxyglutarate, $[\alpha] - 1.72°$ (acetone), in 80% yield.

EXAMPLE 9

The procedure of Example 1 was repeated using the microorganism *Citrobacter freundii* (ATCC 6750) to obtain monoethyl-3(S)-hydroxyglutarate, $[\alpha] + 1.38°$ (acetone) in 60% yield.

EXAMPLE 10

Transformation of (S)-(+)-ethyl hydrogen-3-hydroxyglutarate to (R)-(−)4-amino-3-hydroxybutyric acid. To a solution of ethyl hydrogen β-hydroxyglutarate (1.14 g, $[\alpha]_D = +1.5°$, acetone) in pyridine (6 ml), was added acetic anhydride (0.8 ml) and the mixture stirred under a dry atmosphere for 4 hours. The mixture was diluted with ethyl acetate (75 ml) and washed with water (75 ml). The organic layer was washed with 10% HCl (60 ml), water (25 ml) and brine (25 ml). The aqueous layers were backwashed with ethyl acetate (75 ml) each time. The combined organic solution was dried ($Na_2SO_4$). On removal of the solvent in vacuo, the acetate was obtained as a pale yellow oil (1.282 g), of sufficient purity as judged by nmr spectrum to be directly used in the next step.

To the crude ethyl hydrogen β-acetoxyglutarate (1.282 g) in benzene (18 ml) under argon at ~6° C., was added oxalyl chloride (1.9 ml) over a few minutes. The reaction was allowed to warm up to room temperature and then stirred for 5 hours. The solvent was removed by rotor evaporation and the remaining brown oil pumped for a short while. The brown oil (the acid chloride of ethyl hydrogen β-acetoxyglutarate) was used directly in the next step.

To the solution of the acid chloride in acetone (10 ml) at 0° C., was added a solution of sodium azide (1.3 g) in water (12 ml) over a couple of minutes. The mixture was stirred at 0° C. for 15 min. The ice bath was removed and the mixture stirred for a further 15 min. The mixture was diluted with water (100 ml) and extracted with benzene (2×75 ml). The benzene solution was washed with brine (125 ml), dried ($Na_2SO_4$) and filtered.

The above solution of the azide in benzene was refluxed under a dry atmosphere for ~70 hours. The solvent on removal in vacuo, gave the isocyanate, IR [film, $cm^{-1}$ 2980, 2260, 1740, 1370, 1225, 1030], as a brown oil (1.190 g).

A sample of the isocyanate (730 mg) was charged with 18% HCl (8 ml) and heated at 100°–110° C. (oil bath temp.) for 4 hours. After allowing to stir at room temperature for 18 hours, the water and HCl were removed by rotor evaporation. The crude brown gum was pumped. The product was dissolved in a small quantity of water and applied to a Dowex (1×4, −OH column, length 7 cm, width 2 cm). The column was eluted with water (100 ml), 5% $NH_4OH$ (100 ml) and finally 15% $NH_4OH$ (1500 ml). Evaporation of the 15% $NH_4OH$ eluate gave (R)-(−)-4-amino-3-hydroxybutyric acid as a white crystalline solid (172 mg, pure by nmr spectrum). The overall yield of the product from ethyl hydrogen β-hydroxy glutarate corresponds to 36.4% ($[\alpha]_D = -16.9°$, $H_2O$).

In the foregoing Example the hydroxy group was protected through acylation (reaction of ethylhydrogen β-hydroxyglutamate with acetic anhydride in pyridine solvent), a reaction and protective mechanism well known in the art. Also, if desired, protection for the hydroxy group can be obtained via etherification, as through the addition of an alkylsilyl or tetrahydropyranyl group, instead of by acylation, as is also well known in the art. Thus, before subjecting the optically-active monester (β-hydroxyglutaric monoester) to rearrangement the hydroxyl function can be protected in the process of this invention by either the acylation or etherification mechanism.

I claim:

1. A method for preparing optically active 4-amino-3-hydroxybutyric acid which comprises subjecting a β-hydroxyglutaric diester having the formula $RO_2CCH_2$—$CHOHCH_2CO_2R$, where R is selected from the group consisting of $CH_3$ and $CH_2CH_3$, to asymmetric hydrolysis by exposing it to the fermentative action of the carboxyesterase enzyme elaborated by a microorganism selected from the genera consisting of Arthrobacter, Corynebacterium, Acinetobacter, Citrobacter, Mycobacterium and Rhodococcus and recovering the corresponding optically-active β-acyloxy glutaric monoester protecting the hydroxyl function present in said monoester subjecting the thus protected monoester to rearrangement to obtain the corresponding isocyanate subjecting said isocyanate to alkaline hydrolysis and recovering optically-active 4-amino-3-hydroxybutyric acid.

2. The method of claim 1 wherein R is $CH_3$.
3. The method of claim 1 wherein R is $CH_2CH_3$.
4. The method of claim 1 wherein the rearrangement is carried out via the Curtius rearrangement.
5. The method of claim 1 wherein the rearrangement is carried out via the Hofmann reaction.
6. The method of claim 1 wherein the rearrangement is carried out via the Schmidt rearrangement.
7. A method for preparing optically active 4-amino-3-hydroxybutyric acid which comprises converting ethyl hydrogen β-acetoxyglutarate to its acid chloride by treating said glutarate with an acyl chloride subjecting the thus formed ethyl hydrogen β-acetoxy glutarate acid chloride to rearrangement to obtain the corresponding isocyanate subjecting said isocyanate to alkaline hydrolysis and recovering optically active 4-amino-3-hydroxybutyric acid.

8. The method of claim 7 wherein the rearrangement is through a nitrene intermediate in accordance with the Curtius rearrangement reaction.

9. A compound having the formula

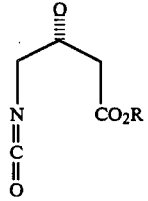

where R is selected from the group consisting of $CH_3$ and $CH_2CH_3$.

* * * * *

UNITED STATES PATENT OFFICE
CERTIFICATE OF CORRECTION

Patent No. 4,584,270          Dated April 22, 1986

Inventor(s) Charles J. Sih

It is certified that error appears in the above-identified patent and that said Letters Patent are hereby corrected as shown below:

In Column 1, the structural formula 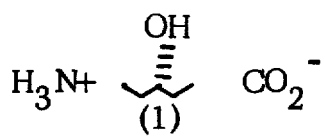 should be

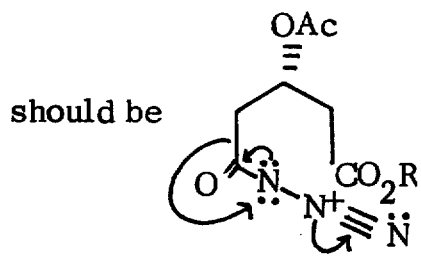

In Column 3, Lines 34 - 41, the structural formula 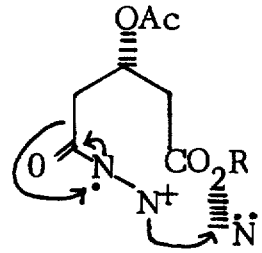

should be 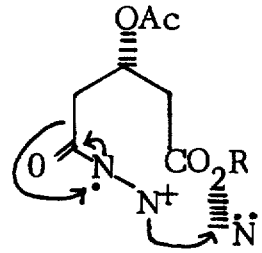

In Column 7, Line 18, before "genera" --group of-- should be inserted.

UNITED STATES PATENT AND TRADEMARK OFFICE
CERTIFICATE OF CORRECTION

PATENT NO. : 4,584,270

DATED : April 22, 1986

INVENTOR(S) : Charles J. Sih

It is certified that error appears in the above-identified patent and that said Letters Patent is hereby corrected as shown below:

In Column 8, Claim 9, the structural formula 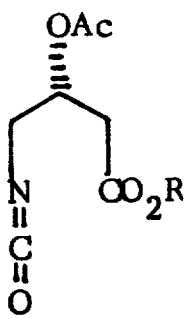

should be 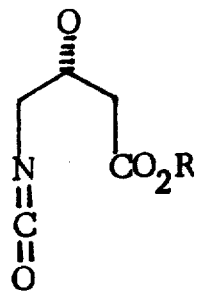

Signed and Sealed this

Nineteenth Day of August 1986

[SEAL]

Attest:

DONALD J. QUIGG

*Attesting Officer*        *Commissioner of Patents and Trademarks*